United States Patent [19]

Gardner

[11] 4,208,352
[45] Jun. 17, 1980

[54] OXIDATION PROCESS FOR ALKYLAROMATICS

[75] Inventor: Lloyd E. Gardner, Bartlesville, Okla.

[73] Assignee: Phillips Petroleum Company, Bartlesville, Okla.

[21] Appl. No.: 640,591

[22] Filed: Dec. 15, 1975

[51] Int. Cl.$^2$ .............................................. C07C 45/02
[52] U.S. Cl. .................................... 568/431; 568/815; 568/812; 568/808; 562/416
[58] Field of Search ............... 260/618 C, 524 R, 524, 260/599; 568/815, 812, 808; 562/416

[56] References Cited

U.S. PATENT DOCUMENTS

| 2,545,870 | 3/1951 | Baker et al. | 260/618 C X |
| 3,641,157 | 2/1972 | Riegel et al. | 260/599 |
| 3,745,193 | 7/1973 | Riegel et al. | 260/618 C X |
| 3,859,344 | 1/1975 | Shigeyasu | 260/524 R |
| 3,907,881 | 9/1975 | Kuhlmann | 260/524 R |

Primary Examiner—Bernard Helfin

[57] ABSTRACT

A process is provided for oxygenating alkyl-substituted aromatic compounds. Alkyl-substituted aromatic compounds in the liquid phase are contacted with molecular oxygen at a temperature below 200° C. in the presence of a catalyst system which is substantially insoluble in the reaction mixture at reaction conditions. The catalyst components are a suspended copper compound and a suspended bromine compound which preferably are associated with a major quantity of a suitable catalyst support material. Optionally, the reaction can be carried out in the presence of minor amounts of acetic acid, acetic anhydride or suitable inorganic nitrate compounds.

4 Claims, No Drawings

OXIDATION PROCESS FOR ALKYLAROMATICS

BACKGROUND OF THE INVENTION

This invention relates to producing oxygenated products from alkyl-substituted aromatic compounds. In one of its aspects this invention relates to low temperature, liquid phase conversion of alkyl-substituted aromatic compounds to oxygenated products. In another aspect the invention relates to the use of a combination of copper and bromine compounds substantially insoluble in the reaction mixture at reaction conditions as a catalyst for the production of oxygenated products from alkyl-substituted aromatic compounds.

It has heretofore been known that relatively plentiful hydrocarbons can be converted to other less plentiful and therefore more valuable organic compounds by processes such as oxidation. For example, alkyl-substituted hydrocarbons such as toluene have been converted to oxygenated products such as benzaldehyde in vapor phase oxidation processes using various catalyst systems. Still other more recent oxidation processes employ lower reaction temperatures and liquid phase conditions wherein one or more catalyst components are substantially dissolved in the reaction mixture at the reaction conditions.

The present invention provides an alternative liquid phase process for the oxidative conversion of alkyl-substituted aromatic compounds to oxygen-containing products. The process is particularly applicable for producing products in an intermediate stage of oxidation such as aromatic alcohols, ketones or aldehydes. Moreover, the present invention features a catalyst system which is substantially insoluble in the reaction mixture at reaction conditions. Thus, the catalyst or catalyst components can be more readily separated from the reaction mixture and can, in a batch process, be readily returned for continued catalytic use in succeeding batches.

It is therefore an object of this invention to provide a method for converting alkyl-substituted aromatic compounds to oxygenated products using liquid phase contact of the alkyl-substituted aromatic compounds with a suitable catalyst system that is substantially insoluble in the reaction mixture at reaction conditions.

Other objects, aspects and the various advantages of this invention will become apparent upon reading the specification and the appended claims.

STATEMENT OF THE INVENTION

According to the process of the present invention, alkyl-substituted aromatic compounds are converted to oxygenated products in a liquid phase catalytic process wherein the alkyl-substituted feedstock is contacted with molecular oxygen at 50°–200° C. in the presence of a suspended copper compound and a suspended bromine compound. Optionally, the reaction can be carried out in the additional presence of adjuvants such as minor amounts of acetic acid or acetic anhydride or suitable inorganic nitrate compounds. In a preferred embodiment of the present invention the suspended copper and bromine compounds are associated with a major quantity of a suitable catalyst support material.

The alkyl-substituted aromatic feedstocks which can be used as feedstocks for the present invention are those aromatic compounds with oxidizable alkyl substituents. Generally these compounds will correspond to the following generic formulas:

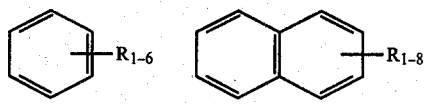

wherein each R is selected from hydrogen, halogen atoms or branched or unbranched alkyl groups having from 1 to about 6 carbon atoms, more usually from 1 to about 4 carbon atoms, at least one R being an alkyl group free of quaternary carbon atoms. Usually, such compounds will contain 1–2 alkyl groups and 0–1 halogen atoms.

Some examples of such suitable feedstocks are: toluene, p-tert-butyltoluene, o-xylene, m-xylene, p-xylene, 1,2,4-trimethylbenzene, 1,3,5-trimethylbenzene, 1,2,4,5-tetramethylbenzene, p-chlorotoluene, ethylbenzene, p-isopropyltoluene, isopropylbenzene, n-butylbenzene, p-propyltoluene, m-bromo-toluene, alpha-methylnaphthalene, beta-isopropylnaphthalene, n-hexylbenzene, and the like and mixtures thereof.

The copper compounds which are used in the catalyst system of the present invention are those which will promote the oxidation of organic compounds and which will form a suspension in the alkyl-substituted feedstock at reaction conditions. Some examples of suitable copper compounds are cupric bromide, cuprous bromide, cupric nitrate, cupric chloride, and the like, and mixtures thereof.

To assist in suspending of the copper compounds in the reaction mixture and to facilitate even more the separability of the catalyst from the reaction mixture, the copper compound can be associated with any suitable solid catalyst support material which is insoluble in the system and which has no deleterious effects. Such catalyst support materials will generally have a surface area of at least about 1 $m^2/g$, preferably 100–250 $m^2/g$. A large number of such catalyst support materials are known and some examples are alumina, silica-alumina, clays, synthetic zeolites, and the like. Alumina is particularly preferred because of its ready availability and because of its effectiveness in the oxidation reaction.

The bromide component of the catalyst system of the present invention is preferably an inorganic bromide such as the alkali metal bromides and also including hydrogen bromide. Of these, lithium bromide has been found particularly effective. When copper bromide is utilized as the copper component, this same compound can also satisfy the bromide requirements. Thus, copper bromide can be both the copper compound and the bromine compound of the present invention.

However, it is frequently desirable to include auxiliary bromide compounds, other than the copper bromide, in the reaction zone. In addition to the alkali metal bromide and hydrogen bromide, organic bromide compounds such as the brominated aromatic and saturated aliphatic compounds having up to about 10 carbon atoms per molecule and up to about 6 bromine atoms per molecule. Presently preferred are compounds having up to 2 bromine atoms attached to aliphatic compounds or radicals. Some examples of suitable organic bromides are benzyl bromide, ethylene dibromide, propyl bromide, and the like, and mixtures thereof.

The nitrate compounds which are suitable for use in the catalyst system of the present invention are generally the inorganic nitrates including the alkali metal nitrates and nitric acid. Also included are compounds which are convertible to inorganic nitrates under the oxidative conditions of the invention process. Some of these are alkali metal nitrites, and oxides of nitrogen such as NO, $NO_2$ and the like. Alkali metal nitrates such as lithium nitrate have been found particularly convenient and effective.

The conditions under which the oxidation process of the present invention is carried out are those conditions of temperature and pressure under which the reaction mixture is substantially in the liquid phase. Generally, the mixture is maintained in the range of about 50° C. to about 200° C., more usually about 150° C. to about 170° C. The partial pressure of oxygen in the system will generally be in the range of about 5 to about 500 psig ($3.4 \times 10^4 - 3.4 \times 10^6$ Pa) more usually about 10 to about 100 psig ($6.9 \times 10^4 - 6.9 \times 10^5$ Pa). Air can be used as a source of oxygen, if desired or the molecular oxygen can be diluted with nitrogen or with other inert gases. The amount of oxygen present within the reaction zone will, in any event, be at least the theoretical amount to oxidize the alkyl groups present to the extent desired and will generally be in excess of that theoretical amount. The process can be carried out either batchwise or continuously and the reaction time will depend upon the specific components of the reaction mixture but will generally be in the range of from about 0.1 to about 30 hours, more frequently about 0.5 to about 10 hours.

The other components of the reaction mixture will generally be present in amounts in terms of millimoles per mole of alkyl-substituted aromatic feedstock which are as follows. Copper, bromide and nitrate compounds are calculated in terms of their ions. A copper compound will be present in an amount from about 0.1 to about 100 millimole/mole and, preferably, will be present in an amount of about 1 to about 50 millimole/mole. A bromide compound will be present in an amount from about 1 to about 1000 millimoles/mole and, preferably, in an amount from about 20 to about 500 millimoles/mole. A nitrate compound can be present in an amount from 0 to about 200 millimoles/mole and, preferably, can be present in an amount from 0 to about 100 millimoles/mole. Acetic acid or acetic anhydride can be present in an amount from 0 to about 100 millimoles/mole and, preferably, from 0 to about 30 millimoles/mole.

If desired, the copper, bromide or nitrate compounds or any combination of these can be incorporated into a suitable solid catalyst support material at concentrations in the range of about 0.1 to about 40 weight percent of the total combination based on the weight of the total composite including support material. It is indicated that any of the commonly used catalyst support materials are suitable for use as the catalyst support in this invention. As will be indicated later alumina is particularly preferred. The supported catalyst can be prepared using any suitable and conventional catalyst forming techniques such as impregnation, dry mixing, and the like. For example, particulate support material or previously pelleted support material can be impregnated with aqueous solutions of the copper, bromide, or nitrate compounds. After impregnation, the supported composition can be dried. After drying the catalysts are ready for use.

In some instances it can be convenient to carry out the reaction in the presence of a diluent. Diluents, such as benzene or chlorobenzene for example, which are liquid, inert, and which do not solubilize the catalyst components at reaction conditions can be used. Compounds such as tert-butyl-benzene are not oxidized in this system and can, therefore, be used as a diluent if desired.

After leaving the reaction zone, the reaction mixture can be separated by conventional methods such as by filtration, fractional distillation, etc., to isolate and recover the desired products. Incompletely oxidized products can be recycled as well as other components of the reaction mixture which have not been consumed. The feature of the present invention is that the suspended catalyst system can be readily removed from the reaction mixture such as by filtration, centrifugation, settling, and the like. The separated catalyst, if desired can be reused in the process with or without additional treatment such as washing or drying.

The products which are obtainable by use of the present invention process are those corresponding to the feedstock wherein the alkyl-substituents have been at least partially oxidized to form groups such as alcohol, ketone, aldehyde, acid, or ester groups. The process is particularly effective for producing compounds having aldehyde or alcohol groups. When more than one alkyl substituent is present in the feedstock molecule, some or all of these can be oxidized, at least partially, depending upon the severity of the reaction conditions.

The oxygen-containing aromatic products of the present invention have a wide utility. For example, benzoic acid and benzyl alcohol are articles of commerce, being used in various agricultural, pharmaceutical, and chemical intermediate applications.

Because of the advantages of a suspended and easily separable catalyst system, the total reaction mixture should be such that the catalyst components have no appreciable solubility in it. Thus, the specific ingredients and their specific concentrations of the reaction mixture should be such as to dissolve little or none of the inorganic components of the catalyst. If acetic acid or acetic anhydride is present, their concentrations should be maintained at a level below that which would solubilize the inorganic components. If organic bromides are present, these will generally be soluble and will not, of course, be separable by filtration.

EXAMPLE I

A series of runs was carried out to illustrate the oxidation of p-xylene and other alkylaromatics using the suspended catalyst system of the present invention. Batch reactions of mixtures having the indicated compositions were subjected to the indicated reaction conditions. The batch runs were carried out in a 500 ml glass-lined rocking autoclave. After charging the reactor with the indicated liquid and solid components, the reactor was pressured with 100 psig (at 24° C.) initial oxygen pressure. The initial xylene to $O_2$ mole ratio was about 2.5.

After the reaction period, the reaction mixtures were subjected to separation and analysis procedures which generally included a filtration step to remove the solid catalyst components and an analysis of the organic phase by gas-liquid chromatography. The analyses were reported in area percent and the conversion of the feedstock and the selectivity to specific products were computed from these analyses.

The essential conditions and results of these runs are shown in Table I.

TABLE I

OXIDATION OF ALKYLAROMATICS

| Run No. | 1 | 2 | 3 | 4 | 5 | 6 | 7 | 8 | 9 | 10 |
|---|---|---|---|---|---|---|---|---|---|---|
| Temp. °C. | 150 | 150 | 150 | 150 | 150 | 150 | 150 | 150 | 150 | 150 |
| Time, hrs. | 2.0 | 4.0 | 3.0 | 6.4 | 5.0 | 4.0 | 4.0 | 4.0 | 4.0 | 4.0 |
| Charge | | | | | | | | | | |
| p-xylene, g | 43.1 | | | 17.3 | 17.2 | 17.2 | 34.6 | 35.0 | 35.0 | 35.0 |
| Toluene, g | | 43.3 | | | | | | | | |
| p-Tertiary-butyltoluene, g | | | 42.7 | | | | | | | |
| Chlorobenzene, g | | | | 55.3 | | | | | | |
| PTBB, g | | | | | 34.7 | 34.7 | 10.0 | 10.0 | 10.0 | 10.0 |
| $Ac_2O$, g | | | | | | | | 2.2 | | 2.2 |
| LiBr, g | 5.0 | 5.0 | 5.0 | 5.0 | 5.0 | 2.0 | 2.0 | 2.0 | 2.0 | 2.0 |
| $CuBr$, g | 1.0 | 1.0 | 1.0 | 1.0 | 1.0 | 1.0 | 1.0 | 1.0 | 1.0 | 1.0 |
| $LiNO_3$; g | 1.0 | 1.0 | 1.0 | 1.0 | 1.0 | 1.0 | 1.0 | 1.0 | | |
| $O_2$, psig (initial) | 100 | 100 | 100 | 100 | 100 | 100 | 100 | 100 | 100 | 100 |
| Conv. % | 20 | 1 | 20 | 17 | 15 | 14 | 18 | 20 | 19 | 23 |
| Prod. Dist., % | | | | | | | | | | |
| Aldehyde | 88.3 | | 58.4 | 48.3 | 31.1 | 31.8 | 46.6 | 35.2 | 56.1 | 32.9 |
| Alcohol | 1.8 | | 6.6 | 19.5 | 19.2 | 20.6 | 20.2 | 13.6 | 23.5 | 16.8 |
| Acid | 3.8 | | | 11.1 | 36.0 | 32.1 | 15.0 | 13.5 | 7.7 | 18.2 |
| Bromo | 0.6 | 90 | 0.6 | 0.7 | | 0.4 | 0.7 | 3.5 | 1.0 | 3.4 |
| Diaryls | 5.5 | 10 | | | | | | | | |
| Bromide | | | 34.4 | 19.2 | 12.3 | 12.7 | 11.6 | 8.1 | 7.1 | 6.4 |
| Acetate | | | | | | | | 24.1 | | 20.8 |
| Other | | | | 1.2 | 1.4 | 2.4 | 6.0 | 2.1 | 4.6 | 1.6 |

The data in Table I illustrate that several alkylaromatics can be converted to oxidation products in a liquid phase reaction in which the catalyst components are suspended and from which the catalyst components can be filtered. Runs 4–10 were carried out in the presence of varying amounts of a diluent which had essentially no solubilizing effect on the catalyst components. The presence of the diluent in these runs facilitated the handling and transfer of the reactor contents. Runs 1–3 contained no such diluent and, therefore, diluents such as ether and/or benzene were added to the reactor contents after the reaction period to facilitate removal of the reaction mixture from the reactor.

Runs 7–10 illustrate that the presence of a nitrate catalyst component is optional, its effect being to modify the product distribution. Similarly, the presence of acetic anhydride is also seen to be optional, its presence serving to increase conversion slightly and modify the product distribution. Run 2 indicates that the conversion of toluene is more difficult in this system than the conversion of p-xylene. No significant toluene conversion was obtained under these conditions in the absence of minor amount of acetic anhydride (see conversion of toluene in later Examples in the presence of minor amounts of acetic anhydride).

EXAMPLE II

Preparation of $CuBr_2/LiBr/Al_2O_3$ (Catalyst A)

A 100 g quantity of eta-alumina (Davison 1/16 inch extrudates) was impregnated with an aqueous solution prepared by dissolving 100 g LiBr and 50 g $CuBr_2$ in distilled water and diluting to 250 ml. The alumina was soaked for two hours in this solution and the excess solution was then poured off. The alumina absorbed 56 ml of the solution.

The wet catalyst pellets were then dried under a heat lamp and then heated in a furnace at 210° C. for 3 hours. Each gram of the completed catalyst retained about 0.1927 g Cu.

EXAMPLE III

Preparation of $CuBr_2/LiBr/LiNO_3$ (Catalyst B)

In a manner similar to that of Example I 50 g of the same 1/16 inch extrudates were soaked in an aqueous solution containing 0.4 g/ml LiBr, 0.2 g/ml $CuBr_2$ and 0.1 g/ml $LiNO_3$. The alumina extrudates absorbed 25 ml of the solution in 2 hours. The extrudates were then dried under a heat lamp and heated 3 hours at 195° C.

EXAMPLE IV

Preparation of $CuBr_2/Al_2O_3$ (Catalyst C)

In a manner similar to that of Example II, 50 g of the same eta-alumina 1/16 inch extrudates were soaked in 250 ml of an aqueous solution containing 50 g $CuBr_2$. The extrudate absorbed 34 ml of the solution in 2 hours. The extrudates were then dried and heated in a furnace for 3 hours at 200° C. The completed catalyst contained about 12.6 weight percent $CuBr_2$.

EXAMPLE V

Preparation of $CuBr_2/SiO_2$-$Al_2O_3$ (Catalyst D)

In a manner similar to that of Example II, 41.16 g of a 24–48 mesh silica-alumina (Houdry cracking catalyst) was impregnated by soaking in an aqueous 250 ml solution containing 50 g $CuBr_2$. The excess solution was poured off, the catalyst absorbing about 78 ml of the solution. After drying and heating in a muffled furnace, the finished catalyst contained 20.7 weight percent of the $CuBr_2$ salt.

EXAMPLE VI

Preparation of $CuBr_2$/Zeolite (Catalyst E)

In a manner similar to that of Example II, 55.38 g of 1/8 inch pellets of a synthetic zeolite (Norton Zeolon H) absorbed 19 ml of a 250 ml aqueous solution containing 50 g $CuBr_2$. The pellets were dried and heated in a furnace at 180° C. for 3 hours.

EXAMPLE VII

Preparation of $CuBr_2/Al_2O_3$ (Catalyst F)

In a manner similar to that of Example II, 57.46 g of the eta-alumina 1/16 inch extrudates were soaked in 250 ml of an aqueous solution containing 50 g $CuBr_2$, absorbing 36 ml of that solution. After drying and heating in a furnace for 4 hours at 205° C., the finished catalyst was calculated to contain 10.97 weight percent $CuBr_2$.

EXAMPLE VIII

Preparation of $CuBr_2$/Mole Sieve (Catalyst G)

In a manner similar to that of Example II, 53.12 g of the mole sieve (Linde 13 X) was impregnated by soaking in an aqueous solution containing 0.20 g $CuBr_2$/ml, absorbing 45 ml of the solution. After pouring off the excess solution, the mole sieve was given a water wash, then dried, then heated for 4 hours at 205° C. The finished catalyst was calculated to contain 7.49 weight percent $CuBr_2$.

EXAMPLE IX

Still another series of runs was carried out to illustrate the oxidation of p-xylene and other alkyl aromatics using that embodiment of the present invention wherein the oxidation catalyst components have been deposited on a suitable catalyst support such as alumina. Batch runs were carried out in a 500 ml glass-lined rocking autoclave. After charging the reactor with the indicated liquid and solid components, the reactor was pressured with 100 psig (at 24° C.) initial oxygen pressure.

After the reaction period, the reaction mixtures were subjected to separation and analysis procedures which generally included a filtration step to remove the solid catalyst and an analysis of the organic phase by gas-liquid chromatography. The analyses were reported in area percent and the conversion of the feedstock and the selectivity to specific products were computed from these analyses.

In several instances, the same charge of catalyst was used to catalyze a number of batch reactions. This was done simply by separating the solid catalyst particles from the liquid components of the reaction batch and reusing those catalyst particles in a succeeding batch run. In some instances the liquid components were merely decanted from the catalyst and the wet catalyst was reused. In other instances the separated catalyst was washed with ether and dried before reuse. In still other instances, the separated catalyst was subjected to heating at relatively high temperatures, at about 260° C., before being reused.

In this series of runs, the alkylaromatics were oxygenated in systems utilizing Catalyst A or Catalyst B, that is, alumina-supported $CuBr_2$-LiBr or alumina-supported $CuBr_2$-LiBr-$LiNO_3$. The essential conditions and results of these runs are shown in Table II.

TABLE II

OXGENATION OF ALKYLAROMATICS USING
$CuBr_2$—LiBr/$Al_2O_3$ OR $CuBr_2$—LiBr—LiNo 3/$Al_2O_3$ CATALYSTS

| Run No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Temp. °C. | 150 | 150 | 150 | 150 | 150 | 150 | 150 | 150 | 150 | 150 | 150 | 150 | 155 | 160 | 160 |
| Time, Hrs. | 4.0 | 4.0 | 4.0 | 4.0 | 8.3 | 7.0 | 7.0 | 7.2 | 4.0 | 4.0 | 4.0 | 7.8 | 6.5 | 6.5 | 4.0 |
| Charge | | | | | | | | | | | | | | | |
| p-xylene,g | 35.0 | 35.0 | 35.0 | 35.0 | 35.0 | 20.0 | | 35.0 | 35.0 | 35.0 | 35.0 | 35.0 | | | |
| Toluene, g | | | | | | | 30.4 | | | | | | 30.4 | 30.4 | 30.4 |
| PTBB,g | 10.0 | 10.0 | 10.0 | 10.0 | 10.0 | 25.0 | 10.0 | 10.0 | 10.0 | 10.0 | 10.0 | 10.0 | 10.0 | 10.0 | 10.0 |
| $Ac_2O$,g | | | | | | | | | | | | | | | 2.2 |
| Catalyst | A(1)[d] | A(2) | A(3) | A(4) | A(5) | A(1) | A(1) | A(4) | B(1) | B(2) | B(3) | B(4) | B(1) | B(3) | B(1) |
| Cat., g | 15.7 | 21.9[b] | 24.8[b] | 15.0[c] | 15.7 | 15.7 | 21.9[b] | 17.3 | 25.6[b] | 27.7[b] | 30.6[b] | 17.3 | 25.6[b] | 15.0 | |
| $OCH_2Br$,g | | | | | | | | | | | | | | | |
| $EtBr_2$, g | | | | | | | | | | | | | | | |
| $O_2$, psig (initial) | 100 | 100 | 100 | 100 | 100 | 100 | 100 | 100[a] | 100 | 100 | 100 | 100 | 100 | 100 | 100 |
| Conv., % | 17 | 13 | 12 | 12 | 11 | 17 | 9 | 26 | 15 | 12 | 7 | 18 | 12 | 12 | 22 |
| Prod. Dist., % | | | | | | | | | | | | | | | |
| Aldehyde | 47.2 | 49.0 | 76.7 | 47.7 | 68.1 | 49.9 | 19.0 | 60.6 | 52.3 | 57.3 | 64.4 | 59.9 | 35.9 | 53.4 | 18.8 |
| Alcohol | 28.7 | 36.8 | 18.5 | 46.8 | 28.1 | 18.9 | 5.5 | 33.3 | 29.1 | 36.3 | 32.5 | 35.0 | 6.1 | 25.8 | 9.7 |
| Acid | | | | | | | | | | | | | 0.3 | 20.8 | 24.4 |
| Bromo | 16.6 | 1.1 | 0.3 | | 0.3 | 22.3 | 64.6 | | 13.6 | 1.3 | 0.4 | | 39.4 | | 8.3 |
| Diaryls | | | | | | | 10.8 | | | | | | 12.5 | | 0.6 |
| Bromide | 0.5 | 1.4 | 1.7 | 2.8 | 1.5 | 2.1 | | 2.1 | | 2.8 | 1.5 | 2.1 | 4.7 | 13.5 | |
| Acetate | | | | | | | | | | | | | | | |
| Other | 7.0 | 11.6 | 2.7 | 2.8 | 1.9 | 6.7 | | 4.0 | 5.0 | 2.3 | 1.3 | 2.8 | 1.4 | | 6.2 |

NOTES:
[a] After 4 hours, reactor cooled to 120° C. and represssured to 121 psig with $O_2$, then reacted another 3.2 hours.
[b] Catalyst (wet) recovered from a previous run merely by decantation.
[c] Catalst recovered from a previous run; was etherwashed and dried.
[d] A(1) indicates fresh catalyst A used first time; A(2) indicates catalyst A recovered from previous run and used for second time; etc.

The data in Table II show that alkylaromatics such as p-xylene or toluene can be oxygenated using the supported catalysts of the present invention under a variety of conditions. Depending upon these conditions, the distribution of the oxygenated products can be varied. The data also show that the supported catalysts can easily be recovered from one run and reused in another with good results.

EXAMPLE X

In a manner largely identical with that of Example IX, another series of runs was carried out to illustrate the operation of still another class of catalysts in the oxygenation of alkylaromatics. This class of catalysts consisted of $CuBr_2$ supported on a suitable catalyst support material.

Essential conditions and results of this series of runs are shown in Table III.

TABLE III

OXYGENATION OF ALKYLAROMATICS USING CuBr$_2$/Al$_2$O$_3$ CATALYSTS

| Run No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Temp., °C. | 150 | 150 | 150 | 150 | 150 | 160 | 150 | 150 | 160 | 160 | 160 | 150 | 150 | 150 | 150 |
| Time, hrs. | 5.8 | 4.0 | 6.0 | 4.0 | 7.0 | 6.0 | 6.8 | 5.5 | 6.0 | 6.5 | 6.5 | 6.0 | 7.0 | 7.0 | 7.2 |
| Charge | | | | | | | | | | | | | | | |
| p-xylene,g | 35.0 | 35.0 | 35.0 | | | | 35.0 | 35.0 | | | | | 35.0 | 35.0 | 35.0 |
| Toluene,g | | | | | 30.4 | 30.4 | | | 30.4 | 30.4 | 30.4 | 30.4 | | | |
| Ethylbenzene,g | | | | 35.0 | | | | | | | | | | | |
| PTBB,g | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| Ac$_2$O,g | | | | | | 1.1 | | | 2.2 | 2.2 | 2.2 | 1.1 | | | |
| Catalyst | C(1)$^d$ | E(2) | C(1) | C(5) | C(6) | C(2) | D(1)$^f$ | E(2)$^g$ | F(1) | F(4) | F(5) | F(3) | F(6) | F(7) | G(1)$^h$ |
| Cat.,g | 20.0 | 29.4$^a$ | 15.0 | 19.2$^b$ | 26.6$^a$ | 16.9$^b$ | 15.0 | 21.1$^b$ | 15.0 | 20.2$^b$ | 18.9$^c$ | 19.6$^b$ | 19.8$^b$ | 17.6$^b$ | 15.0 |
| OCH$_2$Br,g | 2.0 | | | | | 1.0 | | | 2.0 | 2.0 | 2.0 | 1.0 | 1.0 | 0.2 | 1.0 |
| EtBr$_2$,g | | | 2.0 | 1.0 | 1.0 | | 1.0 | 1.0 | | | | | | | |
| O$_2$, psig (initial) | 100 | 100 | 100 | 100 | 100 | 100 | 100 | 100 | 100 | 100 | 100 | 100 | 100 | 100 | 100 |
| Conv., % | 24 | 14 | 24 | 25 | 13 | 18 | 19 | 14 | 21 | 11 | 19 | 12 | 13 | 1 | 4 |
| Prod. Dist.,% | | | | | | | | | | | | | | | |
| Aldehyde | 55.7 | 52.1 | 45.8 | 2.2 | 72.5 | 39.6 | 16.4 | 47.2 | 21.3 | 17.8 | 18.0 | 27.8 | 46.6 | | |
| Alcohol | 16.4 | 21.6 | 18.2 | 20.2 | 8.6 | 15.7 | | 12.1 | 4.9 | 4.9 | 5.6 | 9.8 | 21.6 | | |
| Acid | 13.1 | 24.1 | 19.2 | 2.9 | 15.0 | 32.8 | 1.3 | 24.9 | 17.8 | 25.0 | 38.2 | 25.9 | 28.8 | | |
| Bromo | | | 10.5 | | 1.3 | 0.7 | 63.0 | | 11.1 | 4.9 | 6.8 | 8.3 | | | |
| Diaryls | 5.9 | | | | 2.6 | 2.2 | | 11.9 | 6.8 | 2.1 | 4.7 | 5.0 | | | |
| Bromide | | | | | | 1.5 | | 0.7 | 1.3 | 22.4 | 6.7 | 6.9 | | | |
| Acetate | | | | | | 7.5 | 19.2 | | 24.8 | 22.3 | 19.2 | 16.3 | 2.9 | | |
| Other | 8.9 | 2.1 | 6.3 | 74.8$^e$ | | | | 3.4 | 12.1 | 0.8 | 0.2 | | | | |

NOTES:
$^a$Catalyst (wet) recovered merely by decantation from a previous run.
$^b$Catalyst recovered from a previous run; was etherwashed and dried.
$^c$Catalyst recovered from a previous run; was heated at 260° C. for 3 hours.
$^d$C(1) indicates fresh catalyst C used first time; C(2) indicates catalyst C recovered from a previous run and used a second time; etc.
$^e$Of the 74.8%, 71.2% is selectivity to the ketone, acetophenone.
$^f$Catalyst supported on silica-alumina instead of alumina.
$^g$Catalyst supported on zeolite instead of alumina.
$^h$Catalyst supported on mole sieve instead of alumina.

The data in Table III show that the supported CuBr$_2$ catalyst is also effective for the oxygenation of several alkylaromatics under a variety of conditions. The data also indicate that the oxygenation system can operate with the copper bromide as the only source of bromide ion but that the reaction rate is increased by the presence of supplementary bromides such as benzylbromide or ethylene dibromide. The presence of minor amounts of acetic anhydride also appear to increase the rate at which toluene is oxygenated.

The data also show that several other supports, such as silica-alumina, zeolite mole sieve, etc., can be substituted for the alumina catalyst support. However, the alumina support is seen to be most effective in that it produces the greatest conversion in a given reaction time.

EXAMPLE XI

In a manner similar to that of the preceding examples, several other alkylaromatic compounds were subjected to the oxygenation process of the present invention. In largely qualitative runs, compounds such as p-cymene, p-tertiary-butyltoluene, and alpha-methylnaphthalene were converted to at least small amounts of oxygenated products.

I claim:

1. A process for converting alkyl-substituted aromatic compounds to oxygenated products, said process comprising contacting alkyl-substituted aromatic compounds chosen from those corresponding to the generic formulas:

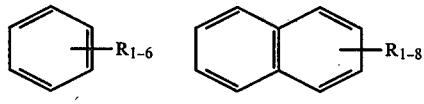

wherein each R is selected from hydrogen, halogen atoms or branched or unbranched alkyl groups having from 1 to about 6 carbon atoms, at least one R being an alkyl group free of quaternary carbon atoms, in the liquid phase at a temperature in the range of about 50° C. to about 200° C. with molecular oxygen in the presence of (1) a catalyst system consisting essentially of a copper compound and a bromine compound, said catalyst system being substantially insoluble in the reaction mixture at reaction conditions, (2) an inorganic nitrate compound present in an amount up to about 200 millimoles per mole of alkyl-substituted feedstock and (3) a compound chosen from the group consisting of acetic anhydride and acetic acid which is present in an amount of up to about 100 millimoles per mole of alkyl-substituted feedstock.

2. A process of claim 1 wherein the copper and bromide compounds are incorporated into a suitable solid catalyst support material at concentrations in the range of about 0.1 to about 40 weight percent of the total of the copper or bromine compounds based on the weight of the total composition.

3. A process of claim 1 wherein the copper is present as a compound in the range of about 0.1 to about 100 millimoles/mole of alkyl-substituted aromatic feedstock and said bromide compound is present in an amount ranging from about 1 to about 1000 millimoles/mole of alkyl-substituted feedstock.

4. A process of claim 1 wherein said alkyl-substituted aromatic compounds contain from 1 to 2 alkyl groups and 0 to 1 halogen atoms.

* * * * *